(12) United States Patent  
Chen

(10) Patent No.: US 8,837,714 B1  
(45) Date of Patent: Sep. 16, 2014

(54) EARPIECE-ORIENTED STERILIZING DUSTPROOF DEVICE

(71) Applicant: Hypervision Tech Co., Ltd., Taipei (TW)

(72) Inventor: Lin-Sze Chen, Taipei (TW)

(73) Assignee: Hypervision Tech Co., Ltd., Taipei (TW)

( * ) Notice: Subject to any disclaimer, the term of this patent is extended or adjusted under 35 U.S.C. 154(b) by 0 days.

(21) Appl. No.: 13/945,636

(22) Filed: Jul. 18, 2013

(51) Int. Cl.
*H04M 1/00* (2006.01)
*H04R 1/12* (2006.01)
*H04M 1/17* (2006.01)
*A61L 2/10* (2006.01)

(52) U.S. Cl.
CPC . *H04R 1/12* (2013.01); *H04M 1/17* (2013.01); *A61L 2/10* (2013.01)
USPC .......................................... 379/452; 379/439

(58) Field of Classification Search
USPC .............. 379/452, 439, 451, 437; 250/492.1, 250/459.11, 455.11
See application file for complete search history.

(56) References Cited

U.S. PATENT DOCUMENTS

| | | | | |
|---|---|---|---|---|
| 6,490,351 | B1* | 12/2002 | Roberts | 379/452 |
| 2002/0162972 | A1* | 11/2002 | Pleet | 250/492.1 |
| 2008/0067418 | A1* | 3/2008 | Ross | 250/455.11 |

* cited by examiner

*Primary Examiner* — Tuan D Nguyen
(74) *Attorney, Agent, or Firm* — C. G. Mersereau; Nikolai & Mersereau, P.A.

(57) ABSTRACT

An earpiece-oriented sterilizing dustproof device includes an earpiece rack body, two swing door bodies, a casing, and a sterilization light source module. The earpiece rack body comprises an upper base, a lower base, and a connection element. The connection element is disposed between the upper base and the lower base. The upper base, the lower base and the connection element define a receiving space. The swing door bodies are pivotally connected to two ends of the earpiece rack body, respectively. The swing door bodies conceal the receiving space. The casing is disposed on the lower base and has two opposing transparent oblique surfaces corresponding in position to the swing door bodies, respectively. The sterilization light source module is disposed at the lower base and inside the casing. Therefore, the earpiece-oriented sterilizing dustproof device is dustproof and disinfects ear pads of on-ear earpieces.

20 Claims, 8 Drawing Sheets

EARPIECE-ORIENTED STERILIZING DUSTPROOF DEVICE

FIELD OF THE INVENTION

The present invention relates to sterilizing dustproof devices for use with earpieces, and particularly for sterilizing on-ear earpieces.

BACKGROUND OF THE INVENTION

People can audition videos and audios in public venues, such as shops which sell multimedia videos and audios. Similarly, individuals and students can take audio courses at libraries, audiovisual classrooms, language learning classroom, and cram schools. To prevent mutual interference between different users and to offer crystal clear audio quality, the aforesaid venues usually provide on-ear earpieces for users.

However, simple wiping and cleaning processes can be performed on the aforesaid public on-ear earpieces only during breaks at libraries, audiovisual classrooms, language learning classrooms, cram schools, and shops. As a result, the on-ear earpieces are used by multiple users consecutively and thus are rife with bacteria during the majority of its service session. Furthermore, housing pads of on-ear earpieces are in direct contact with the skin on the ears as well as the hair of each user who wears the on-ear earpieces and thus serve as a vehicle of germs, thereby posing a threat to the users' health. In addition, if on-ear earpieces are left unused and unsheltered for a long period of time, dust will accumulate on the on-ear earpieces readily and thus render the cleaning process more difficult.

Accordingly, it is imperative to invent an earpiece-oriented sterilizing dustproof device for sterilizing the housing pad of an on-ear earpiece and preventing accumulation of dust.

SUMMARY OF THE INVENTION

It is an objective of the present invention to provide an earpiece-oriented sterilizing dustproof device for sterilizing the housing pad of an on-ear earpiece, enclosing the on-ear earpiece entirely, and making the on-ear earpiece dustproof.

Another objective of the present invention is to provide an earpiece-oriented sterilizing dustproof device whereby the on-ear earpiece can be held in place.

In order to achieve the above and other objectives, the present invention provides an earpiece-oriented sterilizing dustproof device comprising an earpiece rack body, two swing door bodies, a casing, and a sterilization light source module. The earpiece rack body comprises an upper base, a lower base, and a connection element. The connection element is disposed between the upper base and the lower base. The upper base, the lower base and the connection element define a receiving space. The swing door bodies are pivotally connected to two ends of the earpiece rack body respectively. The swing door bodies conceal the receiving space. The casing is disposed on the lower base and has two opposing transparent oblique surfaces corresponding in position to the two swing door bodies respectively. The sterilization light source module is disposed at the lower base and inside the casing.

Regarding the earpiece-oriented sterilizing dustproof device, the swing door bodies each comprise a curved portion, and both two ends of the upper base and two ends of the lower base comprise a curved surface corresponding in position to the curved portion.

Regarding the earpiece-oriented sterilizing dustproof device, the curved portion is defined by a quarter arc, and the curved surface is defined by a half arc corresponding in position to the quarter arc of the curved portion.

The earpiece-oriented sterilizing dustproof device further comprises a plurality of springs connected between the upper base and the swing door bodies, respectively and/or between the lower base and the swing door bodies, respectively, wherein locations at which the springs are fixed to the upper base and the lower base and locations at which the springs are fixed to the swing door bodies, respectively, are different from a center of rotation of each of the swing door bodies.

Regarding the earpiece-oriented sterilizing dustproof device, either, except the transparent oblique surfaces, an outer frame in the casing is opaque and metallic or the casing is entirely transparent.

The earpiece-oriented sterilizing dustproof device further comprises a control panel disposed at the upper base. The control panel comprises a display unit and a switch. The switch is a touch switch or a mechanical switch.

Regarding the earpiece-oriented sterilizing dustproof device, the lower base comprises at least a notch. The at least a notch is obliquely disposed on the top surface of the lower base to bend and extend to a lateral side of the lower base.

The earpiece-oriented sterilizing dustproof device further comprises a sensor and an indicator. The sensor is connected to the swing door bodies. The indicator is connected to the sensor.

Regarding the earpiece-oriented sterilizing dustproof device, the sterilization light source module comprises an annular lamp, a U-shaped lamp, a planar lamp, or a tubular lamp.

Regarding the earpiece-oriented sterilizing dustproof device, the lateral shape of the swing door bodies matches the lateral outline of the casing.

Accordingly, an earpiece-oriented sterilizing dustproof device of the present invention is characterized in that: swing door bodies are pivotally connected to two ends of an earpiece rack body, respectively; after opening the swing door bodies, a user can put on-ear earpieces on a casing easily; housings of the on-ear earpieces can rest on the transparent oblique surfaces of the casing flatly and properly; and, after the swing door bodies have been shut, not only are the on-ear earpieces protected against dust, but housing pads of the on-ear earpieces also admit light and thereby undergo sterilization.

BRIEF DESCRIPTION OF THE DRAWINGS

Objectives, features, and advantages of the present invention are hereunder illustrated with specific embodiments in conjunction with the accompanying drawings, in which.

DETAILED DESCRIPTION OF THE PREFERRED EMBODIMENTS

Figure 1:
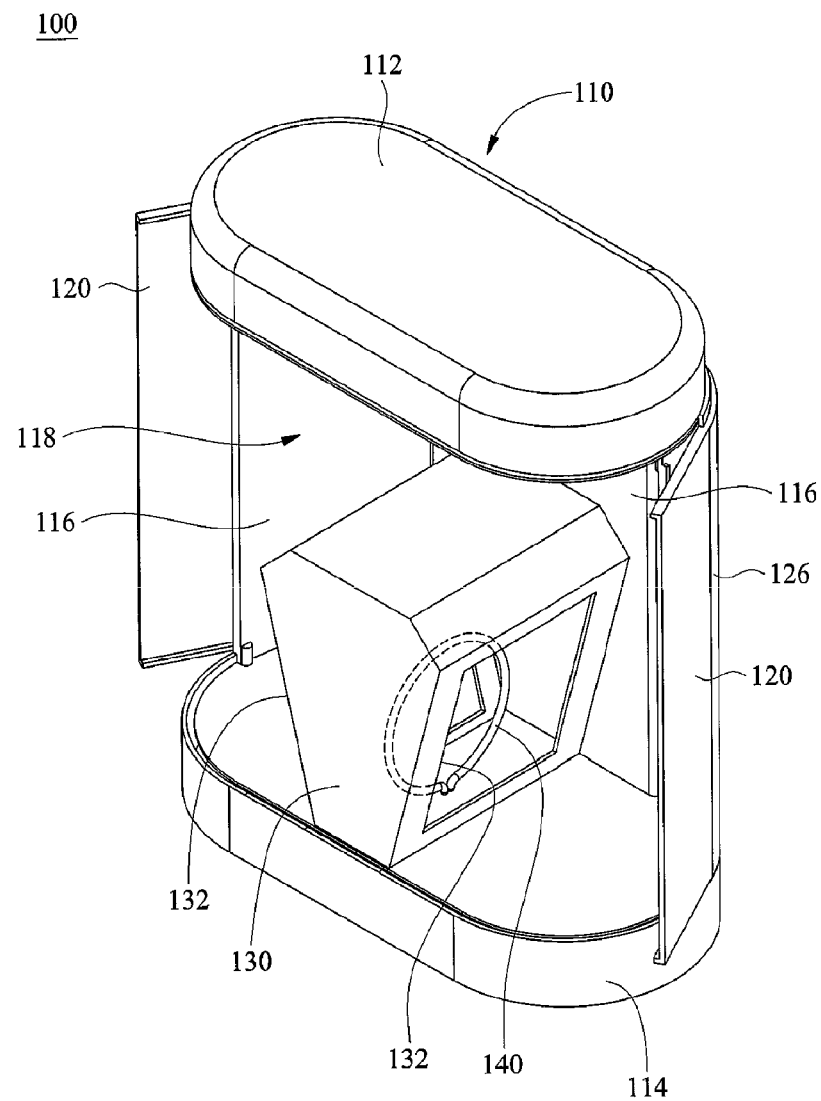
FIG. 1 is a schematic perspective view of an earpiece-oriented sterilizing dustproof device according to a specific embodiment of the present invention.
Figure 2:
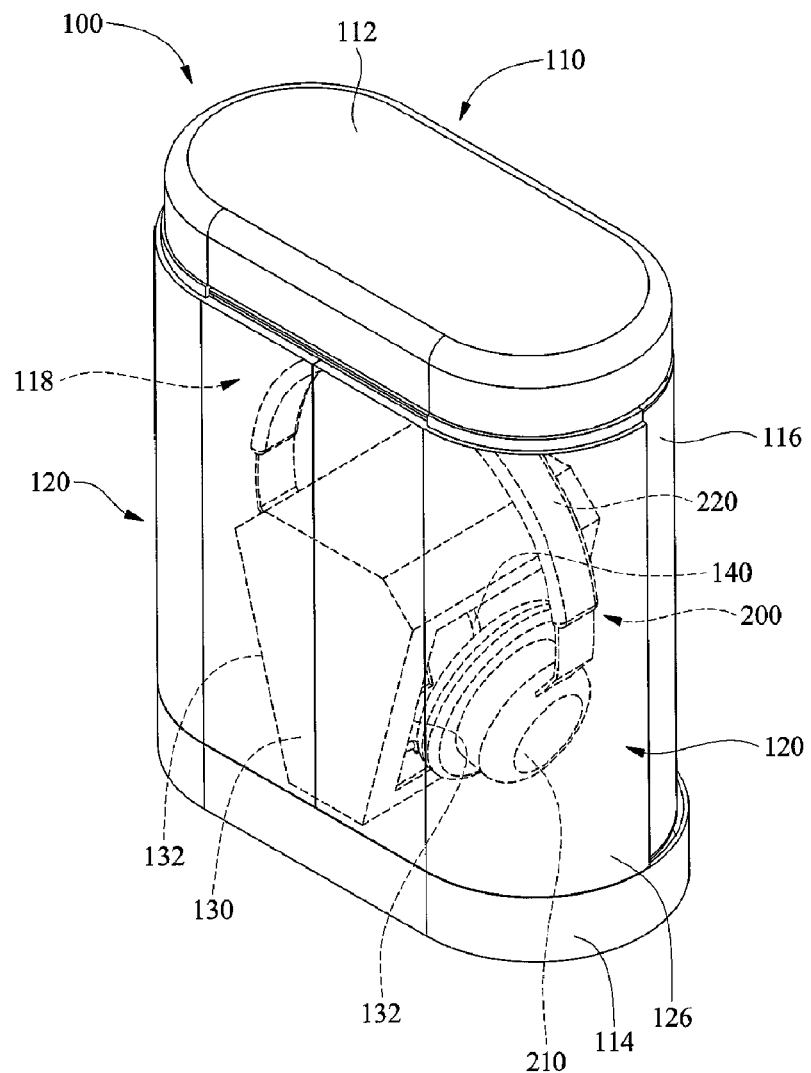
FIG. 2 is a schematic perspective view of operation of the earpiece-oriented sterilizing dustproof device according to the specific embodiment of the present invention.
Figure 3:
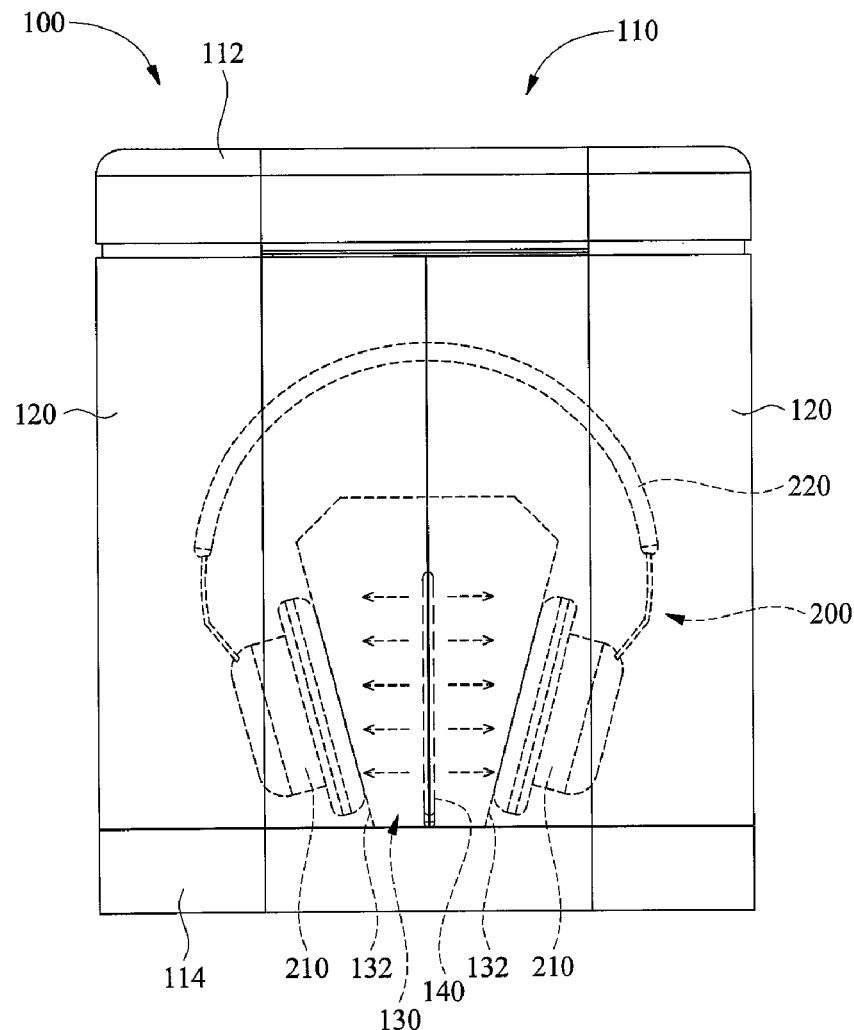
FIG. 3 is a schematic front view of the earpiece-oriented sterilizing dustproof device according to the specific embodiment of the present invention.

Referring to FIG. 1 through FIG. 3, there are shown in FIG. 1 a schematic perspective view of an earpiece-oriented sterilizing dustproof device according to a specific embodiment of the present invention, in FIG. 2 a schematic perspective view of operation of the earpiece-oriented sterilizing dustproof device according to the specific embodiment of the present invention, and in FIG. 3 a schematic front view of the earpiece-oriented sterilizing dustproof device according to the specific embodiment of the present invention. As shown in the diagrams, an earpiece-oriented sterilizing dustproof device 100 comprises an earpiece rack body 110, two swing door bodies 120, a casing 130, and a sterilization light source module 140. The earpiece-oriented sterilizing dustproof device 100 is applicable to an on-ear earpiece 200 with a housing 210.

The earpiece rack body 110 comprises an upper base 112, a lower base 114, and a connection element 116. The connection element 116 is disposed between the upper base 112 and the lower base 114. The upper base 112, the lower base 114 and the connection element 116 define a receiving space 118. The receiving space 118 receives the on-ear earpiece 200.

The swing door bodies 120 are pivotally connected to two ends of the earpiece rack body 110, respectively. The swing door bodies 120 conceal the receiving space 118.

The casing 130 is disposed on the lower base 114. The casing 130 has two opposing transparent oblique surfaces 132. The transparent oblique surfaces 132 correspond in position to the swing door bodies 120, respectively. The transparent oblique surfaces 132 abut against the inner sides of the housings 210 of the on-ear earpieces 200, respectively.

The sterilization light source module 140 is disposed at the lower base 114 and inside the casing 130.

In this embodiment, the sterilization light source module 140 emits sterilizing light (such as UV-C) which penetrates the transparent oblique surfaces 132 to fall on the housings 210 abutting against the transparent oblique surfaces 132 so as to perform sterilization. The sterilization light source module 140 comprises an annular lamp, a U-shaped lamp, a planar lamp, or a tubular lamp. The transparent oblique surfaces 132 each include quartz glass or meshy metallic plate, such that the sterilizing light of the sterilization light source module 140 is emitted out of the casing 130.

After swinging the swing door bodies 120 outwards from the two ends of the earpiece rack body 110 to two sides of the earpiece rack body 110, respectively, a user puts the on-ear earpieces 200 in the receiving space 118 in a manner that the on-ear earpieces 200 straddles the casing 130. As a result, a headband 220 of the on-ear earpieces 200 is positioned between the top side of the casing 130 and the upper base 112. Therefore, the housings 210 clamp the transparent oblique surfaces 132 and are attached thereto. Since the housings 210 of the on-ear earpieces 200 vary in flexibility, the transparent oblique surfaces 132 which are oblique serve the following purpose: the user can rest the housings 210 on the transparent oblique surfaces 132 flatly and properly without bending and pulling the housings 210 of the on-ear earpieces 200 away from each other; and, due to the resilience of the headband 220 of the on-ear earpieces 200, the on-ear earpieces 200 clamp the casing 130 and therefore allow the housings 210 to be positioned on the transparent oblique surfaces 132 of the casing, respectively, in order to admit light.

After putting the on-ear earpieces 200 in the earpiece-oriented sterilizing dustproof device 100, the user shuts the swing door bodies 120 completely, such that the swing door bodies 120 conceal the receiving space 118. Afterward, either the earpiece-oriented sterilizing dustproof device 100 starts automatically or the user starts the earpiece-oriented sterilizing dustproof device 100 manually in order to begin sterilization.

Specifically speaking, referring to FIG. 2 and FIG. 3, the earpiece-oriented sterilizing dustproof device 100 is disposed on a desk (not shown) or is hung on a wall (not shown), and then the user puts the on-ear earpieces 200 in the earpiece-oriented sterilizing dustproof device 100. With the transparent oblique surfaces 132 spacing the housings 210 apart, the sterilization light source module 140 is disposed between the housings 210. After putting the on-ear earpieces 200 in the earpiece-oriented sterilizing dustproof device 100, the user starts the sterilization light source module 140 to cause the sterilization light source module 140 to emit the sterilizing light which eventually falls on the housings 210, so as to disinfect the housings 210 abutting against the transparent oblique surfaces 132 of the casing 130, respectively. Upon completion of sterilization, if the use of the on-ear earpieces 200 is not instantly required, the on-ear earpieces 200 need not be removed from the earpiece-oriented sterilizing dustproof device 100; that is, the earpiece-oriented sterilizing dustproof device 100 can continue to hold the on-ear earpieces 200 and prevent dust from being accumulated on the on-ear earpieces 200.

Figure 4:
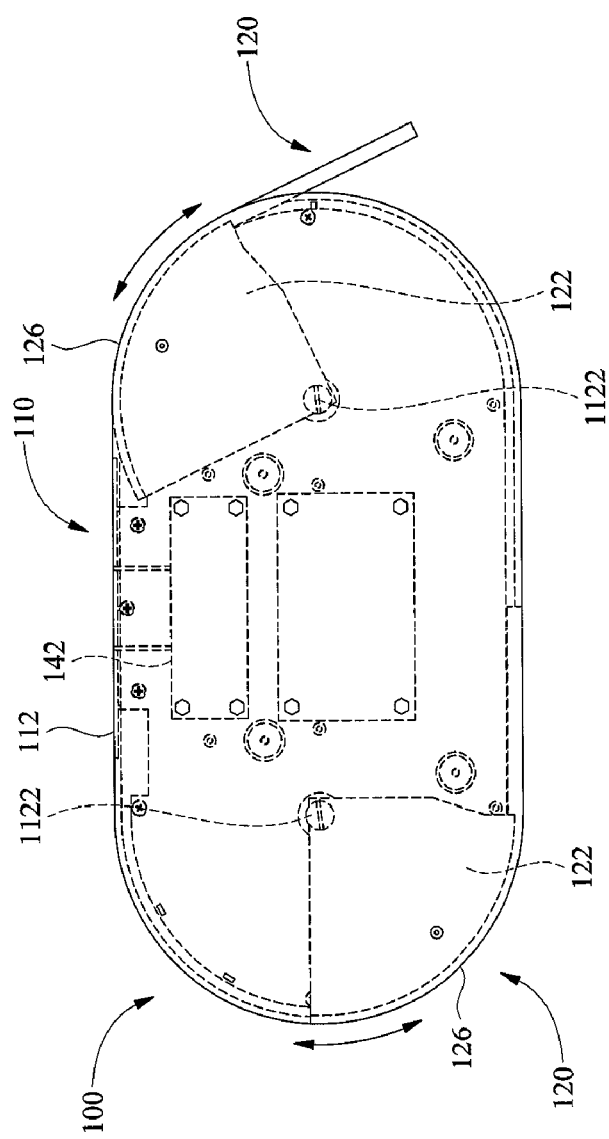
FIG. 4 is a schematic top view of the earpiece-oriented sterilizing dustproof device according to the specific embodiment of the present invention.

Referring to FIG. 4, the swing door bodies 120 are pivotally connected to the upper base 112. The swing door bodies 120 each have a fan-shaped top surface 122 pivotally connected to a pivotal connection portion 1122 of the upper base 112. Hence, to open the swing door bodies 120, the user treats the pivotal connection portions 1122 as the centers of rotation of the swing door bodies 120 and swings the swing door bodies 120 toward two sides of the earpiece rack body 110, respectively. Specifically speaking, the right swing door body 120 swings counterclockwise to open, whereas the left swing door body 120 swings clockwise to open, thereby exposing the receiving space 118. To shut the swing door bodies 120, the user treats the pivotal connection portions 1122 as the centers of rotation of the swing door bodies 120 and swings the swing door bodies 120 toward the other two sides of the earpiece rack body 110, respectively. The right swing door body 120 swings clockwise to shut, whereas the left swing door body 120 swings counterclockwise to shut, thereby concealing the receiving space 118.

In this embodiment, a circuit board 142 connected to the sterilization light source module 140 is disposed in the upper base 112 and then connected via a power line to the sterilization light source module 140 so as to control the operation of the sterilization light source module 140.

Figure 5:
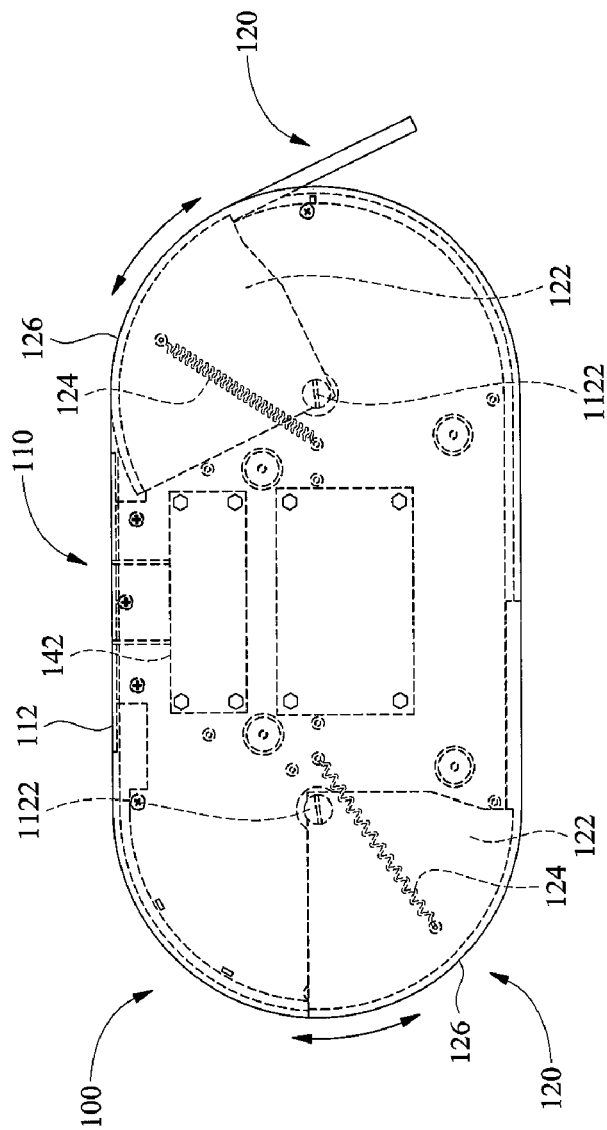
FIG. 5 is a schematic top view of the earpiece-oriented sterilizing dustproof device according to the specific embodiment of the present invention.

In an embodiment, as shown in FIG. 5, the earpiece-oriented sterilizing dustproof device 100 further comprises a plurality of springs 124 (exemplified by two springs 124 in this embodiment.) The springs 124 are each connected between the upper base 112 and the swing door bodies 120, respectively, and/or between the lower base 114 and the swing door bodies 120, respectively. The springs 124 are each fixed to the upper base 112. The position of the lower base 114 and the positions on the swing door bodies 120 to which the springs 124 are fixed are different from the positions of the centers of rotation of the swing door bodies 120. Specifically speaking, referring to FIG. 5, with the springs 124 each being connected only between the upper base 112 and the swing door bodies 120, respectively, the positions of the springs 124 fixed to the upper base 112 are arranged along the line joining the pivotal connection portions 1122. When the swing door bodies 120 are completely opened or completely shut, the springs 124 are of their original length substantially. If the swing door bodies 120 have not yet been completely opened or shut, the springs 124 will be stretched; meanwhile, under the restoring force of the springs 124, the swing door bodies 120 swing in the directions required to shut or open the swing door bodies 120 completely, that is, the springs 124 contract to restore their original length and cause the swing door bodies 120 to be completely opened or shut. In so doing, when it comes to opening the swing door bodies 120, the swing door bodies 120 can be completely opened for certain, such that not only can the on-ear earpieces 200 be smoothly taken out from the earpiece-oriented sterilizing dustproof device 100 or put therein, but the user's hand and the on-ear earpieces 200 are unlikely to hit the swing door bodies 120. Likewise, when it comes to shutting the swing door bodies 120, the swing door bodies 120 can be completely shut for certain, thereby facilitating the subsequent sterilization of the on-ear earpieces 200.

In an embodiment, the swing door bodies 120 each comprise a curved portion 126, whereas two ends of the upper base 112 and two ends of the lower base 114 have a curved surface corresponding in position to the curved portion 126. The curved portion 126 is connected to the fan-shaped top surface 122. Hence, the swing door bodies 120 can move along the periphery of the earpiece rack body 110 entirely so as to be opened and confined to one side of the earpiece rack body 110 or shut and covering the other side of the earpiece rack body 110. As a result, the swing door bodies 120 thus opened and shut are unlikely to invade into the vicinity thereof. That is to say, even if the desktop is crowded, the user can open and shut the swing door bodies 120 smoothly, thereby saving the space for accommodating the earpiece-oriented sterilizing dustproof device 100. Referring to FIG. 5, in this embodiment, the curved portion 126 is defined by a quarter arc, and the curved surface is defined by a half arc corresponding in position to the quarter arc of the curved portion 126; hence, as soon as the swing door bodies 120 are opened, the earpiece-oriented sterilizing dustproof device 100 opens widely in front to allow the user to put the on-ear earpieces 200 in the earpiece-oriented sterilizing dustproof device 100 more easily.

In an embodiment, except the transparent oblique surfaces 132, the outer frame in the casing 130 is opaque and metallic in order to conceal the sterilizing light emitted from the sterilization light source module 140. The sterilizing light within the casing 130 reflects off the metallic outer frame and thereby travels mainly from the transparent oblique surfaces 132 to the housings 210 of the on-ear earpieces 200 to thereby enhance the degree of the sterilization. Furthermore, it is necessary that the swing door bodies 120, the upper base 112, the lower base 114, and the connection element 116 play an auxiliary role in concealing and preventing extra sterilizing light which is not concealed by the casing 130 and the housings 210 from propagating to the surroundings unfavorably.

In other embodiments, the casing 130 is not limited to the disclosure of the present invention, as the casing 130 can be essentially transparent. For instance, the casing 130 is essentially made of quartz glass, such that the sterilizing light generated from the sterilization light source module 140 is emitted out of the casing 130 to fall on multiple portions of the on-ear earpieces 200. For example, the housings 210 of the on-ear earpieces 200 and the headband 220 are irradiated by the sterilizing light, and thus the earpiece-oriented sterilizing dustproof device 100 disinfects multiple portions of the on-ear earpieces 200 simultaneously.

Figure 6:
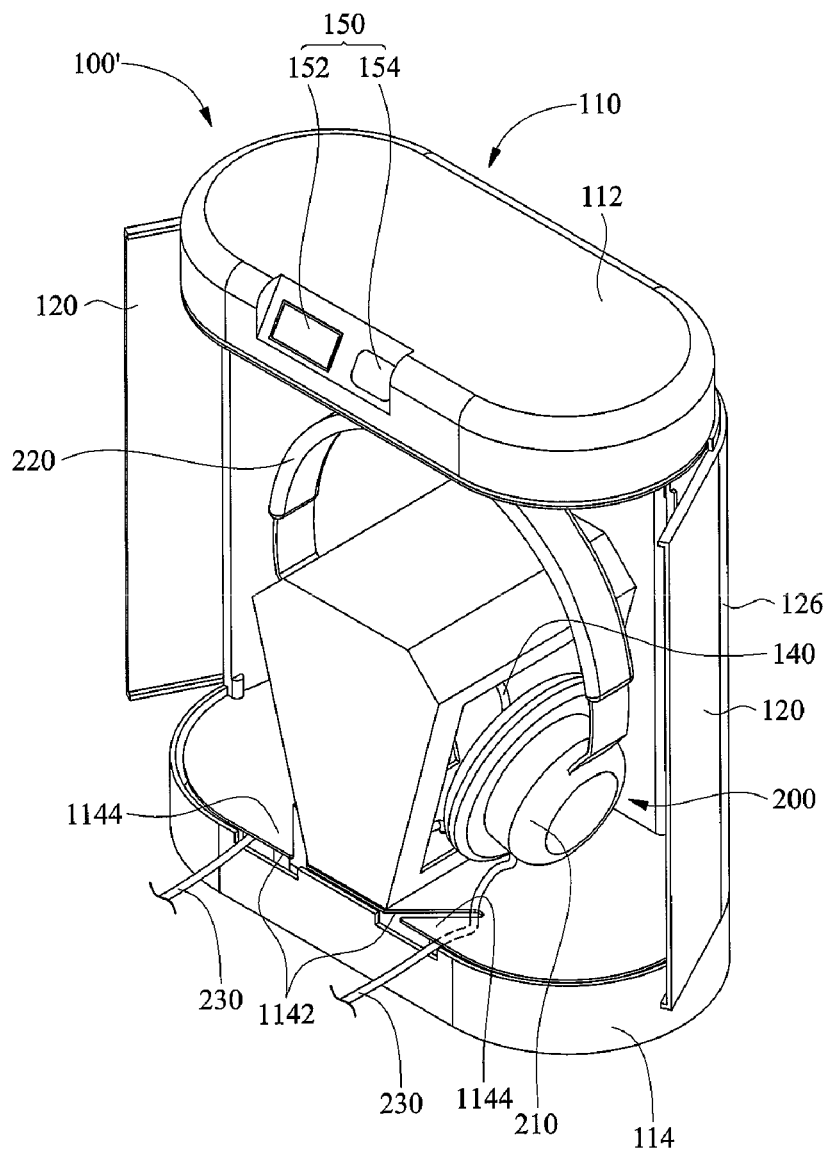
FIG. 6 is a schematic perspective view of operation of the earpiece-oriented sterilizing dustproof device according to another specific embodiment of the present invention.
Figure 7:
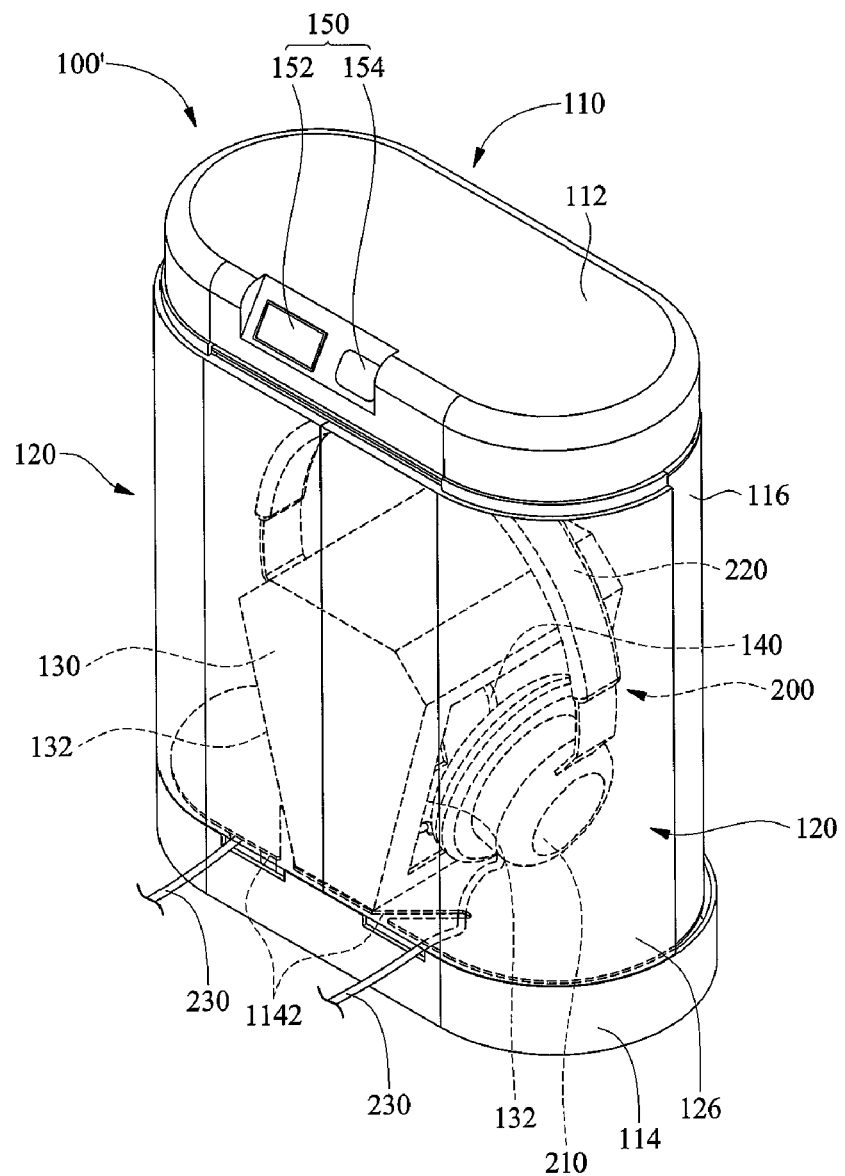
FIG. 7 is a schematic perspective view of operation of the earpiece-oriented sterilizing dustproof device according to the other specific embodiment of the present invention.
Figure 8:
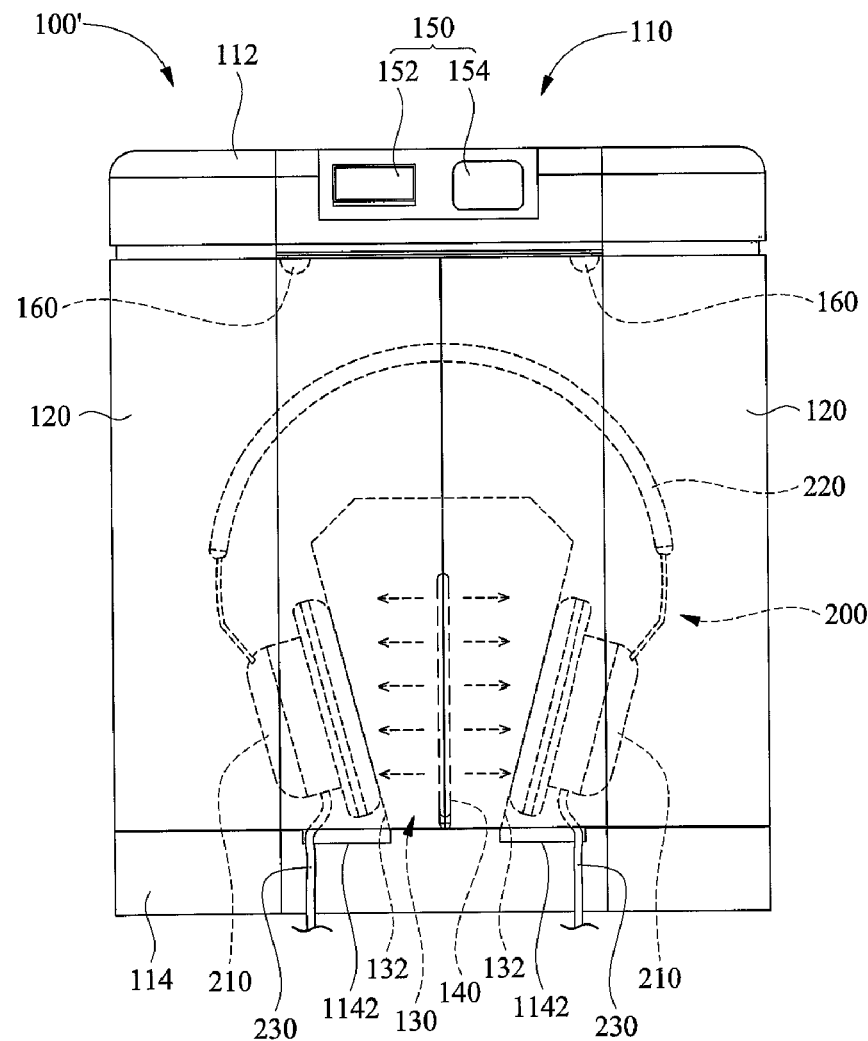
FIG. 8 is a schematic front view of the earpiece-oriented sterilizing dustproof device according to the other specific embodiment of the present invention.

Referring to FIG. 6 through FIG. 8, there are shown in FIG. 6 a schematic perspective view of operation of the earpiece-oriented sterilizing dustproof device according to another specific embodiment of the present invention, in FIG. 7 a schematic perspective view of operation of the earpiece-oriented sterilizing dustproof device according to the other specific embodiment of the present invention, and in FIG. 8 a schematic front view of the earpiece-oriented sterilizing dustproof device according to the other specific embodiment of the present invention. As shown in the diagrams, this embodiment is distinguished from the preceding embodiment in that, in this embodiment, the earpiece-oriented sterilizing dustproof device 100' further comprises a control panel 150 disposed at the upper base 112. The control panel 150 comprises a display unit 152 and a switch 154. The switch 154 is a touch switch or a mechanical switch whereby the user can start and shut down the earpiece-oriented sterilizing dustproof device 100' by means of the switch 154. The display unit 152 displays the current status of the earpiece-oriented sterilizing dustproof device 100, such as "time required for sterilization" and "remaining time", to enable the user to gain insight into the current operation status and sterilization status of the earpiece-oriented sterilizing dustproof device 100' in a real-time manner.

In this embodiment, the lower base 114 comprises at least a notch 1142. The notch 1142 is obliquely disposed on the top surface of the lower base 114 to bend and extend to a lateral side of the lower base 114. The at least a notch 1142 form a triangular baffling plate 1144 on the top surface of the lower base 114. The on-ear earpieces 200 each have a connection line 230. The connection lines 230 of the on-ear earpieces 200 disposed in the earpiece-oriented sterilizing dustproof device 100' can be lifted from the top surface of the lower base 114, inserted into the at least a notch 1142, extended from the lateral side of the lower base 114, and pulled out of the earpiece-oriented sterilizing dustproof device 100'. The connection lines 230 are kept beneath the baffling plate 1144, such that the connection lines 230 are unlikely to be disconnected from the at least a notch 1142 to cause interference; hence, the swing door bodies 120 can still be smoothly opened and shut, thereby dispensing the hassle of putting the connection lines 230 in the earpiece-oriented sterilizing dustproof device 100' while sterilization is underway. The lower base 114 has a hollow core, such that it is easy to form the at least a notch 1142 at the lower base 114 and form the baffling plate 1144.

Referring to FIG. 8, if it is configured that the swing door bodies 120 must be completely shut in order for sterilization to begin for the sake of user safety, then the earpiece-oriented sterilizing dustproof device 100' further comprises a sensor (not shown) and an indicator 160. The sensor is connected to the swing door bodies 120. The indicator 160 is connected to the sensor. The sensor senses and determines whether the swing door bodies 120 are completely shut, for example, detecting whether the swing door bodies 120 are at the positions which indicate that the swing door bodies 120 are completely shut. In this embodiment, the indicator 160 is exemplified by two indicators disposed below the upper base 112 and adapted to illuminate the receiving space 118 or change color to urge the user to check whether the swing door bodies 120 are completely shut.

In another embodiment, the lateral shape of the swing door bodies 120 matches the lateral outline of the casing 130. That is to say, the lateral sides of the swing door bodies 120 are serrate and therefore match the lateral outline of the casing 130. When the swing door bodies 120 are shut, the lateral sides of the casing 130 and the swing door bodies 120 form a smooth surface, and the swing door bodies 120 do not cover the lateral sides of the casing 130, so as to reduce the overall thickness of the earpiece-oriented sterilizing dustproof device 100' and therefore reduce the overall volume of the earpiece-oriented sterilizing dustproof device 100'.

In conclusion, a sterilizing dustproof device of the present invention is characterized in that: swing door bodies are pivotally connected to two ends of an earpiece rack body, respectively; after opening the swing door bodies, a user can put on-ear earpieces on a casing easily; housings of the on-ear earpieces can rest on the transparent oblique surfaces of the casing flatly and properly; and, after the swing door bodies have been shut, not only are the on-ear earpieces protected against dust, but housing pads of the on-ear earpieces also admit light and thereby undergo sterilization.

The present invention is disclosed above by preferred embodiments. However, persons skilled in the art should understand that the preferred embodiments are illustrative of the present invention only, but should not be interpreted as restrictive of the scope of the present invention. Hence, all equivalent variations and replacements made to the aforesaid embodiments should fall within the scope of the present invention. Accordingly, the legal protection for the present invention should be defined by the appended claims.

What is claimed is:

1. An earpiece-oriented sterilizing dustproof device, comprising:
    an earpiece rack body comprising an upper base, a lower base, and a connection element, the connection element being disposed between the upper base and the lower base, wherein the upper base, the lower base, and the connection element define a receiving space;
    two swing door bodies pivotally connected to two ends of the earpiece rack body, respectively, and concealing the receiving space;
    a casing disposed on the lower base and having two opposing transparent oblique surfaces corresponding in position to the swing door bodies, respectively; and
    a sterilization light source module disposed at the lower base and inside the casing.

2. The device of claim 1, wherein the swing door bodies each comprise a curved portion, and both two ends of the upper base and two ends of the lower base comprise a curved surface corresponding in position to the curved portion.

3. The device of claim 2, wherein the curved portion is defined by a quarter arc, and the curved surface is defined by a half arc corresponding in position to the quarter arc of the curved portion.

4. The device of claim 3, further comprising a plurality of springs connected between the upper base and the swing door bodies, respectively and/or between the lower base and the swing door bodies, respectively, wherein locations at which the springs are fixed to the upper base and the lower base and locations at which the springs are fixed to the swing door bodies, respectively, are different from a center of rotation of each of the swing door bodies.

5. The device of claim 3, wherein either, except the transparent oblique surfaces, an outer frame in the casing is opaque and metallic or the casing is entirely transparent.

6. The device of claim 1, further comprising a control panel disposed at the upper base, the control panel comprising a display unit and a switch, the switch being one of a touch switch and a mechanical switch.

7. The device of claim 2, further comprising a control panel disposed at the upper base, the control panel comprising a display unit and a switch, the switch being one of a touch switch and a mechanical switch.

8. The device of claim 5, further comprising a control panel disposed at the upper base, the control panel comprising a display unit and a switch, the switch being one of a touch switch and a mechanical switch.

9. The device of claim 1, wherein the lower base comprises at least a notch, the at least a notch being obliquely disposed on a top surface of the lower base to bend and extend to a lateral side of the lower base.

10. The device of claim 2, wherein the lower base comprises at least a notch, the at least a notch being obliquely disposed on a top surface of the lower base to bend and extend to a lateral side of the lower base.

11. The device of claim 5, wherein the lower base comprises at least a notch, the at least a notch being obliquely disposed on a top surface of the lower base to bend and extend to a lateral side of the lower base.

12. The device of claim 1, further comprising a sensor and an indicator, the sensor being connected to the swing door bodies, and the indicator being connected to the sensor.

13. The device of claim 2, further comprising a sensor and an indicator, the sensor being connected to the swing door bodies, and the indicator being connected to the sensor.

14. The device of claim 5, further comprising a sensor and an indicator, the sensor being connected to the swing door bodies, and the indicator being connected to the sensor.

15. The device of claim 1, wherein the sterilization light source module comprises one of an annular lamp, a U-shaped lamp, a planar lamp, and a tubular lamp.

16. The device of claim 2, wherein the sterilization light source module comprises one of an annular lamp, a U-shaped lamp, a planar lamp, and a tubular lamp.

17. The device of claim 5, wherein the sterilization light source module comprises one of an annular lamp, a U-shaped lamp, a planar lamp, and a tubular lamp.

18. The device of claim 1, wherein a lateral shape of the swing door bodies matches a lateral outline of the casing.

19. The device of claim 2, wherein a lateral shape of the swing door bodies matches a lateral outline of the casing.

20. The device of claim 5, wherein a lateral shape of the swing door bodies matches a lateral outline of the casing.

* * * * *